United States Patent
Murck

(10) Patent No.: US 10,603,297 B2
(45) Date of Patent: Mar. 31, 2020

(54) TREATMENT FOR THERAPY REFRACTORY DEPRESSION

(71) Applicant: Harald Murck, Westfield, NJ (US)

(72) Inventor: Harald Murck, Westfield, NJ (US)

(*) Notice: Subject to any disclaimer, the term of this patent is extended or adjusted under 35 U.S.C. 154(b) by 0 days.

(21) Appl. No.: 16/129,020

(22) Filed: Sep. 12, 2018

(65) Prior Publication Data

US 2019/0099393 A1 Apr. 4, 2019

Related U.S. Application Data

(60) Provisional application No. 62/568,001, filed on Oct. 4, 2017.

(51) Int. Cl.

| | | |
|---|---|---|
| *A61K 31/704* | (2006.01) | |
| *A61K 31/19* | (2006.01) | |
| *A61K 31/215* | (2006.01) | |
| *A61K 36/484* | (2006.01) | |
| *A61P 25/24* | (2006.01) | |
| *A61K 45/06* | (2006.01) | |
| *A61P 3/04* | (2006.01) | |
| *A61P 25/22* | (2006.01) | |
| *A61P 25/28* | (2006.01) | |
| *A61K 31/433* | (2006.01) | |
| *A61K 33/06* | (2006.01) | |
| *A61K 31/22* | (2006.01) | |

(52) U.S. Cl.
CPC ............ *A61K 31/215* (2013.01); *A61K 31/19* (2013.01); *A61K 31/22* (2013.01); *A61K 31/433* (2013.01); *A61K 31/704* (2013.01); *A61K 33/06* (2013.01); *A61K 45/06* (2013.01); *A61P 3/04* (2018.01); *A61P 25/22* (2018.01); *A61P 25/24* (2018.01); *A61P 25/28* (2018.01); *G01N 2800/304* (2013.01); *G01N 2800/52* (2013.01)

(58) Field of Classification Search
CPC .... A61K 31/215; A61K 31/19; A61K 31/704; A61K 36/484
See application file for complete search history.

(56) References Cited

PUBLICATIONS

Seckl Frontiers in Neuroendocrinology 1997, 18, 49-99.*
Ma et al. Toxicology 2011, 285, 83-89.*
Zhou et al. Environmental Toxicology and Pharmacology 2017, 52, 47-53.*
Dhingra et al. Indian Journal of Pharmacology 2005, 37, 390-394.*
Murck et al. Innovations in Clinical; Neuroscience 2015, 12 (3-4 Suppl. A), 26S-40S.*
Eby et al. Magnesium and Major Depression, in Magnesium in the Central Nervous System, Vink, R., Mechifor, M., Eds., University of Adelaide Press, 2011, pp. 313-330.*
Weber J. Lab. Clin. Med. 2003, 142 (2), 71-82.*

* cited by examiner

*Primary Examiner* — Irina Neagu
(74) *Attorney, Agent, or Firm* — Thomas J. Germinario

(57) ABSTRACT

A method treats patient with treatment resistant depression, adjunct to standard antidepressant treatment or as monotherapy. These patients will be identified by non-response to at least one pharmacological antidepressant treatment with a sufficient dose and over a sufficient period of time. Further, one embodiment of the method includes a procedure to identify patients who would benefit from a combination of standard antidepressants with the described compounds from the start of the treatment in order to maximize the likelihood of response. Another embodiment of the method combines the described compounds with forms of Magnesium salts in order to overcome longer term tolerability issues with the compounds. An important downstream mechanism of the described interventions is the property to reduce the production and or increase the absorption of cerebrospinal fluid to treat a variety of symptoms, including cognitive dysfunction, memory loss, apathy, sleep disturbances, pain disorders, and somatoform pain and headache.

22 Claims, No Drawings

TREATMENT FOR THERAPY REFRACTORY DEPRESSION

REFERENCE TO RELATED APPLICATION

This application claims the benefit of the filing date of Provisional Application No. 62/568,001, filed Oct. 4, 2017, which is incorporated herein by reference.

FIELD OF INVENTION

The present invention relates to the field of methods for the treatment of patients suffering from therapy refractory depression and to methods for identifying depressed patients who will benefit from such treatment

BACKGROUND OF THE INVENTION

Depression is a serious and complex disorder affecting millions of people worldwide. In recent years, all approved mediations are based on manipulation the monoaminergic system. However, it is known that the symptoms and neurobiological basis of depression vary considerably.

Currently approved mediations appear to work primarily in patients with a clinical syndrome, with is reflected by a rating on the Hamilton depression rations scale (HAMD) of at least 24 (Kirsch et al. (2008) *PLoS Med* 5(2):e45). This characterization does not, however, point to any specific neurobiological mechanism of depression. Overall the rate of remission with first line antidepressant treatment is only around 30% (Trivedi et al. (2006) *Am J Psychiatry* 163(1): 28-40).

SUMMARY OF THE INVENTION

We describe a method to treat patients with treatment resistant depression and related disorders, adjunct to standard antidepressant treatment or as monotherapy. These patients will be identified by nonresponse to at least one pharmacological antidepressant treatment with a sufficient dose and over a sufficient period of time (6 weeks). Further, one embodiment of the method includes a procedure to identify patients who would benefit from a combination of standard antidepressants with the described compounds from the start of the treatment in order to maximize the likelihood of response.

Another embodiment of the method combines the described compounds with forms of Magnesium salts in order to overcome longer term tolerability issues with the compounds, which are in the center of the invention.

Biological markers for non-response to standard antidepressants have been described in the academic literature, but are not yet included in the diagnosis of specific types of depression and are also not taken up by regulatory authorities. These include clinical signs, like the presence of anxiety or somatization (somatic complaints without clear somatic correlate) and biological markers, including low cortisol levels, high body weight or high body mass index as well as signs of the metabolic syndrome, including insulin resistance (Buttner et al. (2015) *J Psychiatr Res* 66-67:24-37). Therefore, there is a need to identify patients, which do not respond to currently used antidepressants as early as possible and apply a differentiated treatment strategy.

The foregoing summarizes the general design features of the present invention. In the following sections, specific embodiments of the present invention will be described in some detail. These specific embodiments are intended to demonstrate the feasibility of implementing the present invention in accordance with the general design features discussed above. Therefore, the detailed descriptions of these embodiments are offered for illustrative and exemplary purposes only, and they are not intended to limit the scope either of the foregoing summary description or of the claims which follow.

DETAILED DESCRIPTION OF THE PREFERRED EMBODIMENT

In one embodiment, the present invention comprises a treatment of these patients consisting of the administration of a peripheral and/or central acting inhibitor of the enzyme 11-beta hydroxy-steroid-dehydrogenase 2 (11-beta-HSD2) as monotherapy or as a combination therapy to a currently used antidepressant medication.

Examples for compounds from this class are Glycyrrhizic acid (also known as

Glycyrrhizin or Glycyrrhizinic acid) (GZA) or its metabolite glycyrrhetinic acid (GLA) or carbenoxolone. GLA or GZA can be administered as isolated compounds or can be part of natural herbal extracts, for example from glycyrrhiza glabra and related or unrelated plants which contain substances that are active to inhibit 11-beta-HSD2 with or without inhibiting 11-beta-HSD1 in addition.

As a consequence of the peripheral inhibition of 11-beta-HSD2, several physiological effects occur: Cortisol is able to a greater extent to access Mineralocorticoid Receptors (MR) in renal, endothelial and potentially pituitary cells, which otherwise metabolize cortisol quickly and prevent its action at MR. As a consequence, a reduction of the release of aldosterone occurs. This may be related to an increase in sodium (Na+) reabsorption in the kidney, an increase in arterial blood pressure and a reduction in adrenocorticotropic hormone (ACTH) secretion from the pituitary. These changes occur as a consequence of an increased MR-receptor activation by cortisol, in addition and/or alternatively to the physiological ligand aldosterone.

The reduction of the activity of the renin-angiotensin-aldosterone system (RAAS) and in particular the concentration of aldosterone and/or the ratio of the concentration of aldosterone and cortisol has consequences at specific aldosterone sensitive brain areas, including the nucleus of the solitary tract, hippocampus and amygdala (Buttner et al. 2015; Murck et al. (2014) *Nephron Physiol* 128(1-2):17-25). An additional potential consequence is the reduction of the production of cerebrospinal fluid (CSF) in the brain (Weber (2003) *J Lab Clin Med* 142(2):71-82). Therefore, reduction in MR activation has specific actions on brain areas and in addition on cerebrospinal fluid production. Both can in parallel or independently reduce the risk of treatment refractoriness to standard antidepressants.

Therefore, in extension, compounds, which can reduce the production of cerebrospinal fluid are also considered to overcome treatment resistant depression. These are, for example, compounds which inhibit the activity of carbonic anhydrase including acetazolamide, and compounds with secondary activity on carbonic anhydrase activity, including angiotensin II receptor antagonists, calcium channel blockers and MR antagonists (Puscas et al. (1999) *Res Commun Mol Pathol Pharmacol* 105(3):213-36; Puscas et al. (2001) *Drugs Exp Clin Res* 27(2):53-60; Puscas et al. (2000) *Int J Clin Lab Res* 30(3):119-25). In addition, activation of the RAAS, i.e. increased activity of angiotensin II receptors, leads to an increase in vasopressin (AVP) release. Vasopressin is related to increased intracranial pressure (ICP) in a bi-directional way. It is increased in the CSF (Sorensen et al. (1984) *Ann Neurol* 15(5):435-40); Widmayer et al. (2010) *Neurol Res* 32(10):1021-6) and plasma (Id.) in situations of increased ICP. On the other hand intravenous injection of AVP leads to an increase in ICP (Saladin et al. (1993) *Neurol Res* 15(3):198-203), whereas intracerebroventricular (ICV) administration increases ICP in some animal models (Seckl et al. (1991) *Exp Brain Res* 84(1):173-6; Sorensen et al. (1990) *Neurol Res* 12(2):83-8), but not others (Saladin et al. 1993). Conversely, vasopressin antagonists, in particular those targeting VIA receptors, lead to a reduction of brain oedema and intracranial pressure (Krieg et al. (2015) *N Neurotrauma* 32(4):221-7). Therefore, besides a method to reduce the activity of aldosterone, the downstream activity to reduce vasopressin receptor activation, in particular from the VIA type may be beneficial.

Additional mechanisms involved in cerebrospinal fluid production are also covered under the assumption that the increased volume of the choroid plexus and of cerebral ventricular volume can be reduced by specifically targeting the receptor systems involved. These include, but are not limited to ligands of the cannabinoid receptor CB1 (Aston et al., (2004) *Neuroscience Letters* 364: 40-42), the dopamine D1 receptor (Boyson and Alexander (1990) *Ann Neurol* 27:631-635), and the 5-HT2c receptor (Palacios et al., (2017) *Psychopharmacology* 234:1395-1418.

Another embodiment of the present invention administers a combination of the named compounds with magnesium salts in order to overcome potential tolerability issues or mechanism to reverse the beneficial effect on depression and other CNS related disorders. The magnesium addition is beneficial in order to prevent peripheral effects of endothelial MR activation, in particular depletion of magnesium salts from the body. Therefore, the named compounds or their containing preparations can be used in isolation or preferably in combination with a magnesium preparation, including magnesium-citrate, magnesium oratate, magnesium threonate, magnesium oxide or other preparations. This can be administered as a single preparation or as a therapy combining several preparations. These preparations can be either in solid tablet form or as solutions or other preparations.

Another embodiment of the present invention provides a method for identifying patients who are unlikely to respond to standard antidepressant treatment and most likely to benefit from the described preparations. In particular signs of reduced peripheral or increased central MR activity have been linked to a worse response to standard antidepressant treatment. These can be from a list of clinical signs, including, but not exclusively:

List A:
low systolic blood pressure, possibly orthostatic hypotension
low plasma sodium concentration
high plasma potassium concentration
high plasma magnesium concentration
high aldosterone levels in bodily fluids (for example, plasma, serum, or saliva)
high ratio of aldosterone/cortisol concentration in bodily fluids
low concentration of cortisol in bodily fluids
low heart rate variability
high slow wave sleep (SWS)
salt craving
high salt taste threshold
large cerebral ventricular volume
large volume of the choroid plexus
high intraocular pressure
gait disorder
bladder dysfunction The increase in aldosterone also leads to clinical CNS effects, including, but not exclusively (Buttner et al. 2015; Murck (2017) "Aldosterone Action on Brain and Behavior." Pp. 20 159-79 in *Hormones, Brain, and Behavior* 3rd edition edited by D. W. Pfaff and M. Joels: Oxford: Academic Press; Murck et al. 2014) the following:

List B:
memory dysfunction
cognitive dysfunction
anxiety
somatization
depression
amotivational syndrome
obesity GZA or GLA or related compounds can be used as standardized extracts, as preparations of roots of glycyrrhyca glabra or other plants containing compounds with 11-beta-HSD2 activity. 10 Alternatively carbenoxolone can be used. These compounds can be used as isolated compounds or in combination with additional compounds of a combination therapy, for example selective serotonine reuptake inhibitors, (SSRIs), serotonin-noradrenaline-reuptake inhibitors (SNRIs), monoamine-oxidase inhibitors (MAO-inhibitors) and agonists or antagonists of serotonin-noradrenalin and dopamine receptors.

Preparations should contain preferable 1%-100% GZA or GLA. The daily dose should be between 5 mg and 500 mg GLA or GZA, whereas the dose for carbenoxolone is between 10 and 1000 mg. The dose of magnesium-salt, in case a combination therapy is attempted, should be between 50 mg and 5000 mg of Mg2+. Doses of acetazolamide are suggested to be in the range of 50 mg to 5000 mg daily; alternative compounds to reduce CSF production can be utilized in the approved range or a factor 5 higher low lower than the highest and the lowest dose, respectively. For compounds in development the dose needs to be defined.

The present invention provides a method for treating therapy refractory depression. Refractory depression and treatment naive depression with clinical signs or symptoms from List A alone, List B alone or their combination are the preferred target population.

Therefore, the present invention further provides a combination therapy in the treatment of the listed signs and symptoms involving the co-administration of an 11-beta-HSD2 inhibitory preparation with standard drugs which have antidepressant actions including tricyclic and related antidepressants, noradrenaline reuptake inhibitors, serotonin reuptake inhibitors, monoamine oxidase inhibitors and drugs from the class of atypical neuroleptics, either involving the same formulation or the same packaging. Similar mono- or combination therapy can be performed with alternative compounds, which reduce cerebrospinal fluid production, including, but not limited to acetazolamide, ligands of the cannabinoid receptor CB1, ligands of the dopamine receptor D1 and ligands of the serotonin-receptor 5-HT2c.

An additional feature of this invention is to determine the individual dose for a given patient. Because of the interindividual variability of the disease biology is it beneficial to monitor and determine the dose level on the basis of clinical and physiological markers. In particular, an increase of heart rate variability or respiratory sinus rhythm arrhythmia (SRA) is a sign for beneficial CNS activity of the treatment. An increase of these markers should be monitored from time to time. A dose reduction can occur in the case of a reduction of heart rate variability, which may signal a dose, which is too high. Alternative markers indicating a dose in excess of clinical benefit include an increase in SWS and an increase in systolic blood pressure. Ideally, an increase in systolic blood pressure to a high normal range should be achieved. However, an increase in systolic blood pressure and in plasma sodium, as well as a reduction in plasma potassium or magnesium beyond the physiological level should lead to a dose reduction.

EXAMPLES

1. Example 1: An observational study in patients with major depression, who were hospitalized and had some resistance to treatment with standard antidepressants, where observed over a period of up to 42 days. The objective was to test the hypothesis that markers of the activity of the mineralocorticoid receptor (MR) are related to therapy response. Results of a subset of subjects of the still ongoing study found support for the hypothesis: a higher ratio of salivary aldosterone to salivary cortisol (Aldo/Cort-Ratio) as well as a lower systolic blood pressure were related with worse outcome, both of which are in line with the hypothesis that the sensitivity of peripheral MR is correlated to clinical outcome (Buttner et al. 2015). The results of an extension of the study, which includes 46 subjects to complete the observation period, demonstrated differences between responders and non-responders: in responders, but not in non-responders to antidepressant treatment, a significant correlation between the salivary cortisol level and the systolic blood pressure was observed (Pearson Correlation R =0.43, p <0.05 in responders vs. R =−0.29, p >0.2, n. s. in non-responders). Assuming that this effect occurs at the kidney and other peripheral targets this difference is in line with the assumption that a lower activity of the 11-beta-HSD2 exists in responders, as high levels of this enzyme would prevent cortisol to have any effect on MR related parameters, including blood pressure. This finding provides an opportunity to manipulate the system by inhibiting the 11-beta-HSD2, for example with the above mentioned 11-beta-HSD2 inhibitors. This potentially pharmacologically induced inhibition should also lead to a higher systolic blood pressure and a reduced aldosterone secretion, which is suggested to be beneficial in this population.

2. Example 2: Patients have been identified to be non-responders to standard antidepressants on the basis of biomarkers, which indicate a peripheral desensitization of the MR and central overactivity at the MR. As a peripheral MR desensitization is related to an increase in aldosterone, central markers of MR function show an overactivity, i.e. markers of peripheral underactivity and markers of central overactivity characterize this patient population. Markers of peripheral underactivity are a low systolic blood pressure, low peripheral sodium (Na+) concentration in plasma or serum or other body fluids, high potassium (K+) and/or high magnesium (Mg2+) concentrations in these body fluids (Buttner et al. 2015). Increased levels of aldosterone, low levels of cortisol and/or a high aldo/cort ratio are observed in this population. Central mechanisms as a consequence of the increased aldosterone concentration at the MR lead to longer slow wave sleep, lower heart rate variability, higher salt preference and lower salt taste sensitivity in a taste test (Murck et al. 2014). Some or all of these markers will be used to operationalize the selection of patients, who are likely non-responders to standard antidepressants and most likely benefit from an inhibitor of the 11-beta-HSD2 enzyme.

3. Example 3: In addition to the effects of high aldosterone and or low cortisol on specific neuronal activity, both hormones affect the secretion of cerebrospinal fluid: patients with hyperaldosteronism show increased cerebral ventricular volume (McGeeney et al. (2014) *Headache* 54(3):445-58; Sheldon et al. (2015) *Pediatr Res* 77(2):282-9). Therefore, it can be hypothesized that an increased ventricular volume may exist in subjects with higher aldosterone levels or a higher aldo/cort ratio, i.e. those with more treatment refractory depression. We demonstrated in a sub-study, which examined patients with depression, that increased ventricular volume is related to worse response in patients with depression. This was related to signs of increased intracranial pressure in the surrounding anatomical areas, in particular a smaller volume of distinct areas of corpus callosum (CC). This area is also negatively correlated (by trend: p<0.06) with the salivary aldosterone concentration, which is in line with the assumption that higher aldosterone levels lead to pressure on specific CC areas.

4. Example 4: In an observational clinical study in hospitalized patients with depression, several predictive markers for non-response have been described above (Example 1). In addition, we observed difference in biomarker changes in patients responding vs. non-responding to the standard antidepressant treatment. In particular, non-responders showed a significant increase of plasma vasopressin in the course of treatment (p<0.05), which was not observed in responders. In line with the above outlined mechanism, the increase in vasopressin may prevent clinical improvement, potentially via a vasopressin V1A related mechanism. Therefore, Vasopressin V1A antagonists in combination with standard antidepressants or as monotherapy may have therapeutic potential to treat depression.

Although the preferred embodiments of the present invention have been disclosed for illustrative purposes, those skilled in the art will appreciate that many additions, modifications and substitutions are possible, without departing from the scope and spirit of the present 15 invention as defined by the accompanying claims.

5. Example 5: An open label intervention with an extract of Glycyrhizza glabra (active compound approximately 70 mg glyzyrrhizin twice daily) combined with Magnesium citrate (active compound 150 mg twice daily) to characterize biomarker and clinical signs were characterized in the following patient: A 45 year old female patient with her first depression in with the age of 15 and episode duration of 6 month was admitted to the hospital. The patient was treated with a serotonin reuptake inhibitor for a sufficient time before starting the intervention. Several signs and biomarker parameter were regarded as predictive for a non response, based on our earlier observations (Buettner et al., 2015), without the characterized intervention. For female subjects two markers had been identified, i.e. systolic blood pressure and the ratio of the salivary concentrations of aldosterone/cortisol. In this subject a low systolic blood pressure of 116 mm Hg was observed at baseline, in comparison a previously reported threshold for response of 127.5 mmHg or higher; the aldosterone to cortisol ratio was 12.5, which indicates a strong risk of non-response (threshold 0.9 or higher defines non response). The patient had a Hamilton depression Score (21 item version (HAMD-21) of 35 and a HAMD-6 score of 19 at the beginning of the intervention. After two weeks these scores dropped to 29 and 14 respectively, i.e. reduced by 6 and 5 points respectively. As the HAMD-6 identifies the core symptoms of depression it is considered more relevant in this context. In comparison to the data from Buettner et al (2015), which were captured with the same methodology, the expected reduction of the HAMD-6 was 2 points for the overall group (including responders and non responders). The improvement of the patient within 2 weeks of the intervention was considerably more than expected. In parallel the systolic blood pressure rose (within normal limits) to a level of 125 mm Hg, and the saliva aldosterone concentration dropped from 37.5 pg/ml to 22.0 pg/ml. This indicates functional target engagement, i.e. inhibition of the 11-beta-HSD-2. Her overall improvement led her to decide to leave the hospital treatment early in a state of moderate improvement and to continue a follow up treatment, which she had organized herself 6. Example 6: An open label intervention with an extract of Glycyrhizza glabra (active compound approximately 70 mg glyzyrrhizin twice daily) combined with Magnesium citrate (active compound 150 mg twice daily) to characterize biomarker and clinical signs were characterized in the following patient:

A 45 year old patient with a disease duration of major depression for 4 years and an episode duration of 1 year was admitted to the hospital. In male subjects additional biomarkers differentiated responders from non responders, i.e. besides systolic blood pressure and the salivary concentration ratio of aldosterone/cortisol the following markers appears meaningful: heart rate variability, salt taste intensity, salt preference, slow wave sleep duration. His salivary concentration ratio of aldosterone/cortisol at baseline was 9.9 and therefore predictive of non-response. However, his systolic blood pressure was 123 mm Hg, SWS 35 min, HRV 35, all of which are close to the median of the comparison population to distinguish responders from non-responders, and therefore not meaningful. Salt taste intensity was 7 and salt preference 3. Both of these values indicate a high likelihood of response without the intervention. Therefore, the data on outcome prediction were mixed. His HAMD-21 was 42 and his HAMD-6 score was 15 at admission. The patient was treated with a serotonin-noradrenaline reuptake inhibitor. Over 6 weeks of treatment the HAMD-21 dropped to a score of 13 and the HAMD-6 to a score of 5, both indicating response. At the same time the systolic blood pressure remained the same with 123 mm Hg, whereas the plasma sodium concentration showed a slight rise (within normal range) from 140 at baseline to 143 after 6 weeks. Furthermore, the salivary aldosterone concentration showed the expected drop from 27.8 pg/ml to 21.9 pg/ml over the observation period of 6 weeks. This observation indicates that the intervention leads partially to the expected biomarker changes without interfering negatively with the clinical response in a subject, who had an unclear pattern of predictive response markers.

7. Example 7: A healthy subject aged 52 started the intervention for several weeks, and characterized its effect by observing HRV, as determined with a wearable device to capture HRV. The parameter is expressed as "stress level" and is inverse to a HRV measurement. The parameters are captured in intervals of several minutes, but for this purpose the average of this parameter on a week by week basis is sufficient. The overall stress level was calculated as 53 and 54 for the two months before the start of the intervention. Throughout the first 4 weeks of the average stress level was 49 and the dropped rapidly after around 4 weeks of the intervention to a value of 24 for the next month. After discontinuation after 2 month of the intervention levels stayed low at 28 for at least the next 4 weeks, when the recording ended. These findings are in line with the expected reduction of central MR activation with the intervention.

What is claimed is:

1. A method for treating a type of therapy refractory depression, termed mineralocorticoid depression, wherein mineralocorticoid depression is indicated by (A) one or more clinical signs, comprising depression, anxiety, somatization, cognitive dysfunction, memory problems, gait disturbance, obesity or bladder dysfunction, and (B) one or more biomarker signs, as compared to a normal range for a healthy subject, comprising low systolic blood pressure, orthostatic hypotension, low plasma sodium concentration, high plasma potassium concentration, high plasma magnesium concentration, high plasma or saliva aldosterone concentration, high plasma or saliva aldosterone/cortisol ratio, high plasma or saliva vasopressin concentrations, low heart rate variability, high volume of cerebral ventricle, high volume of the choroid plexus, or increased intraocular pressure, and wherein the method comprises administering to a subject in need thereof a preparation comprising a non-toxic first compound having a 11-beta-HSD-2 inhibitory activity, wherein the first compound is selected from the group consisting of glycyrrhizic acid (GZA), glycyrrhetinic acid (GLA), carbenoxolone, and metabolites thereof.

2. The method according to claim 1, wherein the preparation further comprises a second compound which acts to reduce the production of cerebrospinal fluid.

3. The method according to claim 2, wherein the second compound is selected from the group consisting of acetazolamine, angiotensin II receptor antagonists, antagonists of the vasopressin receptor of the V1A type, antagonists of the mineralocorticoid receptor, ligands of the cannabinoid receptor CB1, ligands of the dopamine receptor D1, and ligands of the serotonin receptor from the type 5-HT2c.

4. The method according to any one of claims 1, 2 and 3, wherein the preparation comprises at least 1% GLA or GZA or carbenoxolone or the metabolites thereof.

5. The method according to any one of claims 1, 2 and 3, wherein the preparation is administered at a daily dosage of 5 mg to 500 mg of GLA or GZA.

6. The method according to claim 4, wherein the preparation is administered at a daily dose of 5 mg to 500 mg of GLA or GZA.

7. The method according to any one of claims 1, 2 and 3, wherein the preparation is used in combination with a magnesium compound.

8. The method according to claim 4, wherein the preparation is used in combination with a magnesium compound.

9. The method according to claim 5, wherein the preparation is used in combination with a magnesium compound.

10. The method according to claim 6, wherein the preparation is used in combination with a magnesium compound.

11. The method according to any one of claims 1, 2 and 3, further comprising a procedure for identifying patients suffering from mineralocorticoid depression susceptible to therapeutic benefit from treatment with the preparation, based on A) one or more clinical signs, comprising depression, anxiety, somatization, cognitive dysfunction, memory problems, gait disturbance, obesity, or bladder dysfunction, and B) one or more biomarker signs, as compared to a normal range for a healthy subject, comprising low systolic blood pressure, orthostatic hypotension, low plasma sodium concentration, high plasma potassium concentration, high plasma magnesium concentration, high plasma or saliva aldosterone concentration, high plasma or saliva aldosterone/cortisol ratio, high plasma or saliva vasopressin concentrations, low heart rate variability, high volume of cerebral ventricles, high volume of the choroid plexus, or increased intraocular pressure.

12. The method according to claim 4, further comprising a procedure for identifying patients suffering from mineralocorticoid depression susceptible to therapeutic benefit from treatment with the preparation, based on A) one or more clinical signs, comprising depression, anxiety, somatization, cognitive dysfunction, memory problems, gait disturbance, obesity, or bladder dysfunction, and B) one or more biomarker signs, as compared to a normal range for a healthy subject, comprising low systolic blood pressure, orthostatic hypotension, low plasma sodium concentration, high plasma potassium concentration, high plasma magnesium concentration, high plasma or saliva aldosterone concentration, high plasma or saliva aldosterone/cortisol ratio, high plasma or saliva vasopressin concentrations, low heart rate variability, high volume of cerebral ventricles, high volume of the choroid plexus, or increased intraocular pressure.

13. The method according to claim 5, further comprising a procedure for identifying patients suffering from mineralocorticoid depression susceptible to therapeutic benefit from treatment with the preparation, based on A) one or more clinical signs, comprising depression, anxiety, somatization, cognitive dysfunction, memory problems, gait disturbance, obesity, or bladder dysfunction, and B) one or more biomarker signs, as compared to a normal range for a healthy subject, comprising low systolic blood pressure, orthostatic hypotension, low plasma sodium concentration, high plasma potassium concentration, high plasma magnesium concentration, high plasma or saliva aldosterone concentration, high plasma or saliva aldosterone/cortisol ratio, high plasma or saliva vasopressin concentrations, low heart rate variability, high volume of cerebral ventricles, high volume of the choroid plexus, or increased intraocular pressure.

14. The method according to claim 6, further comprising a procedure for identifying patients suffering from mineralocorticoid depression susceptible to therapeutic benefit from treatment with the preparation, based on A) one or more clinical signs, comprising depression, anxiety, somatization, cognitive dysfunction, memory problems, gait disturbance, obesity, or bladder dysfunction, and B) one or more biomarker signs, as compared to a normal range for a healthy subject, comprising low systolic blood pressure, orthostatic hypotension, low plasma sodium concentration, high plasma potassium concentration, high plasma magnesium concentration, high plasma or saliva aldosterone concentration, high plasma or saliva aldosterone/cortisol ratio, high plasma or saliva vasopressin concentrations, low heart rate variability, high volume of cerebral ventricles, high volume of the choroid plexus, or increased intraocular pressure.

15. The method according to claim 7, further comprising a procedure for identifying patients suffering from mineralocorticoid depression susceptible to therapeutic benefit from treatment with the preparation, based on A) one or more clinical signs, comprising depression, anxiety, somatization, cognitive dysfunction, memory problems, gait disturbance, obesity, or bladder dysfunction, and B) one or more biomarker signs, as compared to a normal range for a healthy subject, comprising low systolic blood pressure, orthostatic hypotension, low plasma sodium concentration, high plasma potassium concentration, high plasma magnesium concentration, high plasma or saliva aldosterone concentration, high plasma or saliva aldosterone/cortisol ratio, high plasma or saliva vasopressin concentrations, low heart rate variability, high volume of cerebral ventricles, high volume of the choroid plexus, or increased intraocular pressure.

16. The method according to claim 8, further comprising a procedure for identifying patients suffering from mineralocorticoid depression susceptible to therapeutic benefit from treatment with the preparation, based on A) one or more clinical signs, comprising depression, anxiety, somatization, cognitive dysfunction, memory problems, gait disturbance, obesity, or bladder dysfunction, and B) one or more biomarker signs, as compared to a normal range for a healthy subject, comprising low systolic blood pressure, orthostatic hypotension, low plasma sodium concentration, high plasma potassium concentration, high plasma magnesium concentration, high plasma or saliva aldosterone concentration, high plasma or saliva aldosterone/cortisol ratio, high plasma or saliva vasopressin concentrations, low heart rate variability, high volume of cerebral ventricles, high volume of the choroid plexus, or increased intraocular pressure.

17. The method according to claim 9, further comprising a procedure for identifying patients suffering from mineralocorticoid depression susceptible to therapeutic benefit from treatment with the preparation, based on A) one or more clinical signs, comprising depression, anxiety, somatization, cognitive dysfunction, memory problems, gait disturbance, obesity, or bladder dysfunction, and B) one or more biomarker signs, as compared to a normal range for a healthy subject, comprising low systolic blood pressure, orthostatic hypotension, low plasma sodium concentration, high plasma potassium concentration, high plasma magnesium concentration, high plasma or saliva aldosterone concentration, high plasma or saliva aldosterone/cortisol ratio, high plasma or saliva vasopressin concentrations, low heart rate variability, high volume of cerebral ventricles, high volume of the choroid plexus, or increased intraocular pressure.

18. The method according to claim 10, further comprising a procedure for identifying patients suffering from mineralocorticoid depression susceptible to therapeutic benefit from treatment with the preparation, based on A) one or more clinical signs, comprising depression, anxiety, somatization, cognitive dysfunction, memory problems, gait disturbance, obesity, or bladder dysfunction, and B) one or more biomarker signs, as compared to a normal range for a healthy subject, comprising low systolic blood pressure, orthostatic hypotension, low plasma sodium concentration, high plasma potassium concentration, high plasma magnesium concentration, high plasma or saliva aldosterone concentration, high plasma or saliva aldosterone/cortisol ratio, high plasma or saliva vasopressin concentrations, low heart rate variability, high volume of cerebral ventricles, high volume of the choroid plexus, or increased intraocular pressure.

19. The method for treating mineralocorticoid depression in a subject in need thereof according to claim 1, comprising co-administering to the subject the first compound with an additional therapeutic agent which is an antidepressant drug.

20. The method for treating mineralocorticoid depression in a subject in need thereof according to claim 1, wherein the first compound is administered to the subject as monotherapy.

21. The method according to claim 19, wherein the first compound and the antidepressant drug are in a single formulation.

22. The method according to claim 19, wherein the first compound and the antidepressant drug are in separate formulations.

\* \* \* \* \*